(12) United States Patent
Dreyer

(10) Patent No.: US 8,756,234 B1
(45) Date of Patent: Jun. 17, 2014

(54) INFORMATION THEORY ENTROPY REDUCTION PROGRAM

(75) Inventor: Keith J. Dreyer, Winthrop, MA (US)

(73) Assignee: The General Hospital Corporation, Boston, MA (US)

( * ) Notice: Subject to any disclaimer, the term of this patent is extended or adjusted under 35 U.S.C. 154(b) by 390 days.

(21) Appl. No.: 10/989,598

(22) Filed: Nov. 16, 2004

(51) Int. Cl.
*G06F 7/00* (2006.01)
*G06F 17/30* (2006.01)
*G06F 19/00* (2011.01)

(52) U.S. Cl.
CPC ................................. *G06F 19/3487* (2013.01)
USPC ........................................................ 707/739

(58) Field of Classification Search
USPC .............................................. 707/6; 705/2, 3
See application file for complete search history.

(56) References Cited

U.S. PATENT DOCUMENTS

| | | | | |
|---|---|---|---|---|
| 6,055,494 A * | 4/2000 | Friedman | ........................... | 704/9 |
| 6,076,088 A * | 6/2000 | Paik et al. | .......................... | 707/5 |
| 6,182,029 B1 * | 1/2001 | Friedman | ........................... | 704/9 |
| 6,292,771 B1 * | 9/2001 | Haug et al. | ......................... | 704/9 |
| 6,556,964 B2 * | 4/2003 | Haug et al. | ......................... | 704/9 |
| 6,738,784 B1 * | 5/2004 | Howes | ................................... | 1/1 |
| 6,757,692 B1 * | 6/2004 | Davis et al. | ................ | 707/104.1 |
| 6,915,254 B1 * | 7/2005 | Heinze et al. | ..................... | 704/9 |
| 7,401,057 B2 * | 7/2008 | Eder | ................................ | 706/20 |
| 7,624,027 B1 * | 11/2009 | Stern et al. | ......................... | 705/2 |
| 2002/0128816 A1 * | 9/2002 | Haug et al. | ......................... | 704/4 |
| 2003/0101056 A1 * | 5/2003 | Howes | ........................ | 704/270 |
| 2003/0105638 A1 * | 6/2003 | Taira | ............................. | 704/275 |
| 2004/0122787 A1 * | 6/2004 | Avinash et al. | ................. | 706/50 |
| 2004/0220895 A1 * | 11/2004 | Carus et al. | ........................ | 707/1 |
| 2004/0243545 A1 * | 12/2004 | Boone et al. | ....................... | 707/2 |
| 2006/0074519 A1 * | 4/2006 | Barker et al. | ................. | 700/213 |

OTHER PUBLICATIONS

Huag et al.; "Computerized Extraction of Coded Fings from Free-Text Radiologic Reports;" Work in Progress; Entrez, PubMed, Radiology, Feb. 1990; 1742(2) 543-8; Abstract only; http://rsna2003.rsna.org/rsna2003/VBK/conference/event_display.cfm?id+66601&em_Id+3800065.

Mannudeep et al; "Application of Innovative Computer Algorithm. LEXIMER, for Automatic Classification of Unstructured Radiology Reports: A Validation Study;" RSNA Conference: Dec. 3, 2003: Abstract only; http://www.ncbi.nlm.nih.gov/entrez/query.fcgl?cmd=Retrieve&db=pubmed&dopt=Abstract&list_uids=2404321.

Dreyer et al; "Application of Innovative Computer Algorithn LEXIMER, for Automatic Classification of Unstructured Radiology Reports: A Validation Study;" RSNA Conference, Chicago, IL; Scientific Papers; Session: Radiology Information; Dec. 3, 2003; 1 sheet (Abstract only).

Dreyer et al.: "Automatic Classiication of Unstructured Radiology Reports, Application of Innovative Computer Algorithm LEXIMER a Validation Study;" slides presented at RSNA Conference, Chicago, IL; Dec. 2, 2003; 18 sheets.

Haug et al.; "Computerized Extratoin of Coded Findings From Free-Text Radiologic Reports. Work in Progress;" National Library of Medicine; PublMed; NCBI; Radiology.Feb. 1990:174(2)543-8; 1 sheet (Abstract only).

* cited by examiner

*Primary Examiner* — Jay Morrison
(74) *Attorney, Agent, or Firm* — Daly, Crowley, Mofford & Durkee, LLP

(57) ABSTRACT

A system and process for automated text analysis which can be used to identify phrases in reports such as medical reports includes identifying a phrase contained within a text, extracting the phrase from the text, determining a value of the phrase and, in response to the phrase having at least a threshold value, reducing the phrase to a root meaning. In one embodiment, the value of the phrase is assigned via lexicon-based hierarchical decision trees.

26 Claims, 6 Drawing Sheets

INFORMATION THEORY ENTROPY REDUCTION PROGRAM

STATEMENTS REGARDING FEDERALLY SPONSORED RESEARCH

Not applicable.

CROSS-REFERENCE TO RELATED APPLICATIONS

Not applicable.

FIELD OF THE INVENTION

This invention relates generally to text processing and more particularly to a system and process for evaluation of clinical findings and recommendations in medical reports.

BACKGROUND OF THE INVENTION

As is known in the art, healthcare institutions are faced with the challenge to demonstrate the appropriateness and accuracy of high cost and high volume medical procedures in general and medical imaging procedures in particular. Utilization management hinges upon the ability to measure the utility of examinations/procedures performed and thus determine the appropriateness of dollars spent.

As is also known, many medical reports, including radiology reports, tend to be unstructured reports. An unstructured report corresponds to a report in which clinical findings and recommendations tend to be embedded and intermingled or interspersed within subjective prose which describes both anatomical and pathological variations in an inconsistent fashion. The current technique for objective classification of unstructured medical findings within reports, including radiology reports, is manual analysis. In particular, to determine whether a medical examination/procedure was appropriate, it is necessary to conduct extensive patient medical chart reviews to determine the appropriateness of the medical examinations/procedures performed. This patient medical chart review process is a manual process and thus is relatively time consuming. Thus, typically relatively small data sets, collected through manual evaluation of report and outcome data, are used to determine the appropriateness of a particular type of medical examination/procedure.

Furthermore, since the process involves individuals reviewing unstructured medical reports, the results are subjective. Moreover, since relatively small data sets are used, it is necessary to extrapolate the small data set to entire ordering practices of individuals and systems as a whole. Reliance on such extrapolation can result in inaccurate conclusions being drawn for a specific medical procedure, medical examination or medical practitioner.

There is currently no automated process to evaluate the findings, recommendations or utilization of relatively high cost medical examinations/procedures via unstructured reports. Since unstructured reports are typically the single result of many high cost diagnostic imaging procedures it is relatively difficult to evaluate utilization of such examinations/procedures. Insurance companies have an interest in evaluating the utilization of high cost medical procedures. Current methods available to insurance and other companies are to simply reduce high cost examinations in a global sense or perform the above-described chart review process to identify and track ordering physicians.

One readily available large scale measure of utilization, the volume of examinations ordered, is found to have questionable correlation to examination volume itself. For example, one medical institution may see an annual increase in certain procedures of 15%. By looking solely at this volume rise, it is very difficult to assume that the increase is due to over-utilization versus a simple increase in the appropriate use of imaging examinations, or what portion correlates to over-utilization at all. However, in the absence of other measures that are independent of volume, such as exam yield and recommendation rate, insurance companies are often left with this single indicator.

It would, therefore, be desirable to provide a system which helps determine the appropriate utilization of high cost medical examinations/procedures. It would also be desirable to provide a system and process which utilizes metrics to evaluate clinical findings and recommendations in unstructured medical reports in general.

SUMMARY OF THE INVENTION

In accordance with the present invention, a process for identifying a phrase contained within a text includes extracting the phrase from the text, determining a value of the phrase and, in response to the phrase having at least a threshold value, reducing the phrase to a root meaning. With this particular arrangement, a process for automated text analysis which can be used to identify phrases in reports such as medical reports is provided. The report can correspond to unstructured medical reports for example. If a phrase is found to have value (i.e. the phrase relates to either a medical finding or a medical recommendation) then the phrase can be associated with the appropriate medical codes. The process can also be used to evaluate the yield of examinations ordered by individual medical practitioners such as physicians.

By assessing each phrase to determine whether the phrase has value, identifying those phrases having at least a threshold value and then subsequently reducing the phrases to their root meanings, it is possible to utilize the phrases deemed to have value to deduce the essence of a text. In conjunction with this technique, a relatively simple method for phrase-level extraction can be performed using standard text parsing and syntactic algorithms. In assessing the value of a certain phrase, the location of the phrase within the text is considered. In some applications, the location of the phrase can weigh heavily on its significance as statements contained within impressions, conclusions, or structured lists tend to summarize lesser statements and thus be of greater value. Therefore, a method to connote phrase position determined at the time of phrase identification and extraction can also be used. In certain applications, extraction of deeper phrase meaning during the data identification and isolation stage is also performed providing even greater insight into the full meaning of a report.

Upon the reduction of information there was observed a second class of phrases that were neither negative nor positive with respect to findings. These phrases represent further action(s) to be taken by the ordering physician at the recommendation of the interpreting radiologist. This knowledge is retained as a separate parameter which is used in further analysis to extract and encoded recommendation of action as well as the timeframe put forth.

The process of the present invention thus provides an automated technique to extract meaning from unstructured medical reports such as radiology reports. The system can process millions of reports very rapidly automatically determining the clinically positive findings, yield, medical advice and recommendation rates for referring physicians, patient cohorts and radiologists. The technique of the present invention can also identify phrases (in some instances entire sentences) which contain information of little or no clinical consequence. It has in accordance with the techniques of the present invention been found that, in many instances, only a minority of the words used within each sentence truly carry the meaning and intent (i.e. information). Thus, the technique of the present invention can be applied to unstructured radiology and other medical reports in such a way that while many details are lost, the implied effect on outcome through the detection of clinically positive findings is preserved and thus available for measure.

In accordance with a further aspect of the present invention, an engine for the evaluation of clinical findings, yield and recommendation in unstructured radiology reports includes with this particular arrangement, a system which identifies radiology reports that represent clinical findings, yield and/or suggested recommendations is produced. The system utilizes automated text analysis to identify phrases in unstructured reports, extract phrases and assess phrasing value. If the phrase is found to have value (i.e. the phrase relates to either a medical finding or a medical recommendation) then the phrase can be associated with the appropriate medical codes. It is further asserted that in the light of new automated measurement techniques whereby payors could evaluate the yield of examinations ordered by individual physicians that they may opt to abandon measuring over-utilization by such inaccurate metrics as examination volume alone.

The system also allows individual ordering physicians to be evaluated against other physicians (or against an average computed from a group of physicians) for lower or higher yield which may, more appropriately, correlate to over and under utilization respectively. Any ordering physicians (following education interventions) could be compared against themselves prior to the educational process to see if the intervention had a positive impact.

The system thus provides an automated method to extract meaning from unstructured medical reports such as radiology reports. The system can process a relatively large number of reports in a relative short period of time while automatically determining clinical findings, yield and recommendation rates for referring physicians, patient cohorts and radiologists. Thus, a system and technique to analyze significance and recommendations of unstructured radiology reports from a large electronic radiology report database, based upon information theory, is provided.

The system and technique identifies and isolates reports, subtracts redundant components and categorizes text based upon its significance (alter care/outcome) and recommendations (for any sort of action). The system and technique can thus be used to analyze and classify radiology and other medical reports into two nonexclusive categories—those that contain clinically significant findings and those that contain recommendations for subsequent action.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Before describing the present invention, some introductory concepts and terminology are explained. A "report" refers to a collection of words in a single document (or electronic file). The words may be grouped as complete sentences or as sentence fragments. The reports can be medical reports (e.g. radiology reports, pathology reports, etc,) or other types of reports (e.g. non-medical reports). In the case of medical reports, the reports are sometimes said to be "unstructured reports." As used herein, the phrase "unstructured report" refers to a report which is comprised of freely structured text. The term "phrases" as used herein refers to a sentence, a sentence fragment or in some cases a single word. A phrase is said to have "value" if the phrase relates to either a medical finding or a medical recommendation. The term "code" as used here in refers to one or more of a plurality of generally accepted medical identifiers (e.g., Current Procedural Terminology, Fourth Revision (CPT4), International Classification of Diseases, Ninth Revision (ICD9), Systematized Nomenclature of Medicine (SNOWMED), RADLEX® and Unified Medical Languages System (UMLS).

The system and techniques of the present invention are sometimes described herein as being used to evaluate unstructured medical radiology reports. It should be appreciated, of course, that the system and techniques are not limited to use with unstructured medical radiology reports. The system and techniques of the present invention can be used to process both structured and unstructured medical and non-medical reports. For example, the system and techniques can be used to perform determining of medical and non-medical reports, to promote structured communication between individuals (including but not limited to medical personnel), to provide input for an alert or notification system, to provide codes used for directed access to medical knowledge, to interface with dictation systems and to provide additional information to users of medical billing systems and to make available codes of additional medical information to system users and to associate codes and other medical information to users of the billing system.

Figure 1:
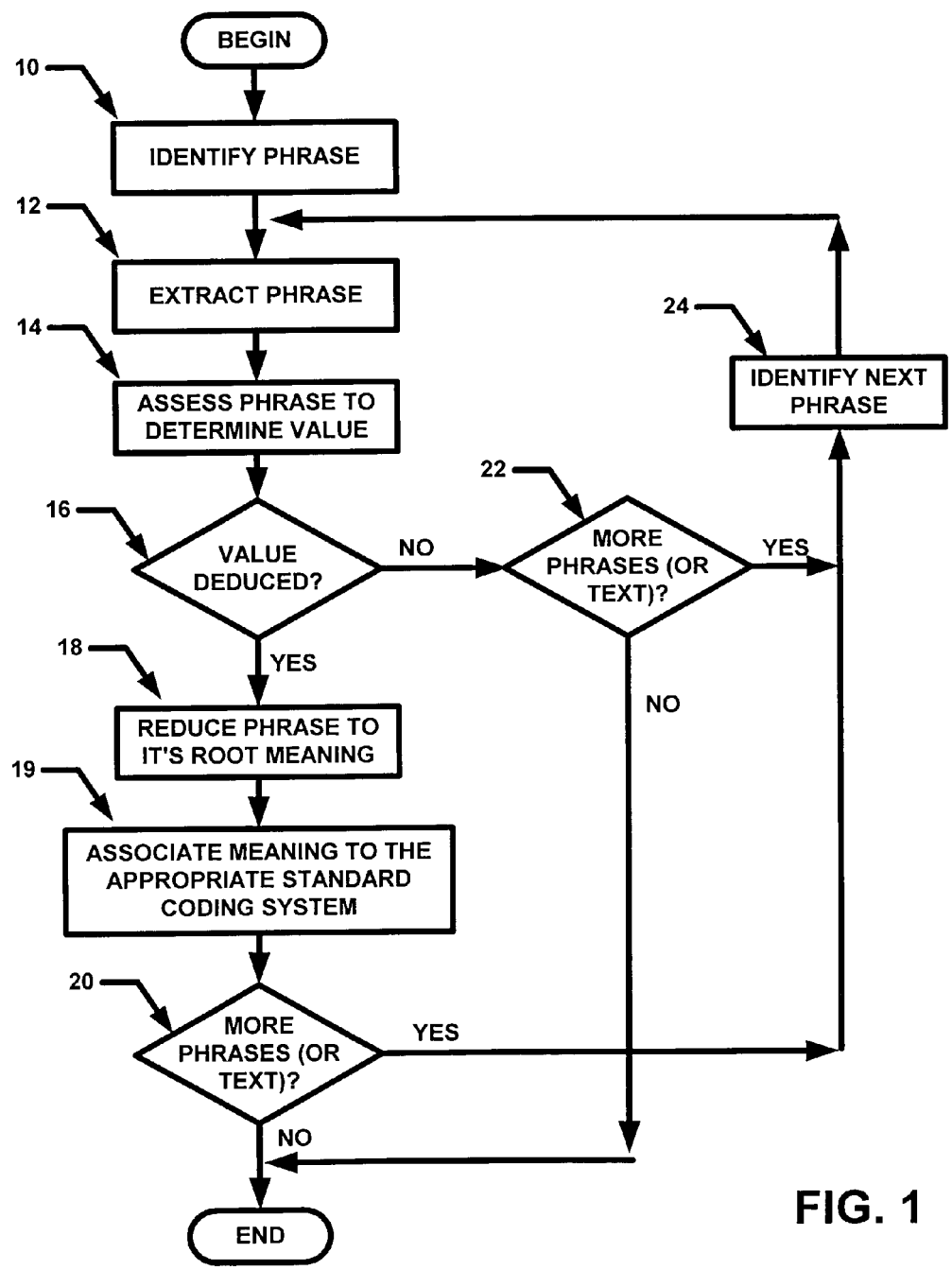
FIG. 1 is a flow diagram of a process for identifying a phrase contained within a text.

FIG. 1 is a flow diagram showing the processing performed by portions of system for processing text. The rectangular elements (typified by element 10 in FIG. 1), are herein denoted "processing blocks" and represent computer software instructions or groups of instructions. The diamond shaped elements (typified by element 16 in FIG. 1), are herein denoted "decision blocks," represent computer software instructions, or groups of instructions which affect the execution of the computer software instructions represented by the processing blocks.

Alternatively, the processing and decision blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required to perform backup and restore operations in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Turning now to FIG. 1, a technique for processing text begins by identifying a phrase in a text as shown in processing block 10. The text may correspond to a medical report or other type of report.

Processing then proceeds to processing block 12 in which the phrase is extracted from the text. The phrase is then assessed to determine if the phrase is considered to have value. This is achieved by evaluating the contents of a phrase for sub-phrases and/or terms contained within a previously trained lexicon of relevant terminology value. Thus, to operate with a particular domain (e.g. radiology or some other particular medical field), a value is assigned to terminology of interest with that domain. In one embodiment, the value is assigned via lexicon-based hierarchical decision trees. If in decision block 16, a decision is made that the phrase does not have value, then processing proceeds to decision block 22.

If a decision is made in decision block 22 that no more text can be processed, then processing ends. If, on the other hand, a decision is made in decision block 22 that more text can be processed, then processing proceeds to processing block 24 in which a next phrase to process is identified and the processing flows again through processing blocks 12 and 14 to decision block 16.

If in decision block 16 a decision is made that the phrase being processed has value, then processing proceeds to processing block 18 where the phrase is reduced to its root meaning. That is, the phrase is distilled to a set of root meanings (or code such a medical codes or codes within a specific field of medicine such as radiology codes) which can be used to represent objective meaning contained within the full report. Codes can then be used to communicate with automated systems for such functions as appropriateness, tabulation, billing, alerts, notification and knowledge searches. Processing then proceeds to processing block 19 in which the meaning of the phrase is associated with the appropriate standard coding system so that a more universal or standard method of communication can be achieved.

Processing then proceeds to decision block 20. If a decision is made in decision block 20 that no more text can be processed, then processing ends. If, on the other hand, a decision is made in decision block 20 that more text can be processed, then processing again proceeds to processing block 24 in which a next phrase to process is identified and the processing again proceeds to processing block 12.

Figure 2:
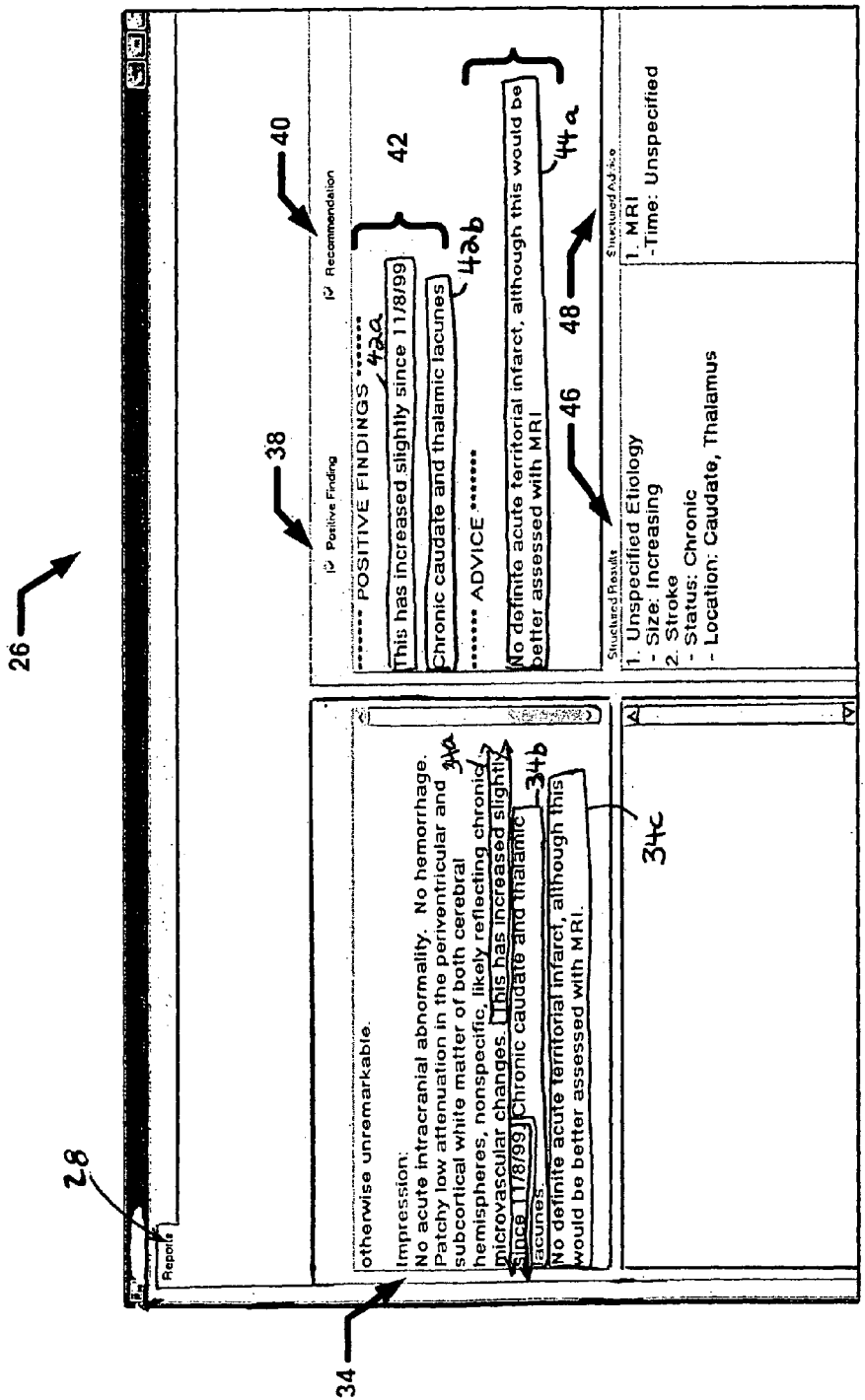
FIG. 2 is a diagrammatic view of a display which shows several fields available to a user of a text processing system.

Referring now to FIG. 2, a screen display 26 of a medical report generated in accordance with the present invention includes a "Reports" tab 28 having a report field 34 containing text which typically corresponds to text dictated by a physician (e.g. via a voice recognition system). A system which utilizes a display such as display 26 thus provides on-line, real-time report generation. It should be noted that field 34 is a scrolling window and that only a portion of the text is visible in field 34 of FIG. 2. It should also be noted that the text provided in field 34 is typically in the form of an unstructured report (e.g. a report in which clinical findings and recommendations tend to be dispersed and intermingled within subjective prose that describes both a patient's anatomical and pathological variations in an inconsistent fashion). Many medical reports, including radiology reports, tend to be in the form of an unstructured report.

The display also includes a positive finding check box 38 and a recommendation check box 40. If checkbox 38 is checked, this indicates that the unstructured text has been analyzed (e.g. via a process such as the process described in conjunction with FIG. 1) and that a positive finding has been identified. If positive finding checkbox 38 is not checked, then no positive finding has been identified. Similarly, if recommendation checkbox 40 is checked, this indicates that unstructured text has been analyzed (e.g. via a process such as the process described in conjunction with FIG. 1) and that a recommendation has been identified and if the recommendation checkbox is not checked, then no recommendation has been identified.

A field portion 42 includes positive findings text. The positive findings text corresponds to text from the report field 34 which identified the finding made by a doctor (or other medical practitioner) in view of any patient examination performed by the doctors and/or any information (e.g. MRI film, other reports, etc. . . . ) provided to the doctor. The LEXIMER system analyzes the text field 34 and extracts phrases from the text which identify a positive finding and places the phrase in the positive finding field 42. This allows a user to view the display 26 and quickly identify the positive finding without having to read the entire unstructured text in field 34.

As can be seen in FIG. 2, item 42a in positive findings field 42 corresponds to item 34a in field 34 and item 42b in field 42 corresponds to item 34b in field 34. Thus, the text in field 42 can be thought of as being the answer to the question: "does the unstructured text in field 34 contain any findings and if so which phrase (or phrases) in the unstructured text corresponds to a finding?"

The LEXIMER system also analyzes the text field in 34 and extracts phrases from the text in field 34 which identify a recommendation and places the phrase in the recommendation field 44. This allows a user to view the display 26 and quickly identify a recommendation made by a physician or other medical practitioner without having to read the entire unstructured text field in 34. Thus, the text in field 44 can be thought of as being the answer to the question: "does the unstructured text in field 34 contain any findings and if so, which phrase (or phrases) in the unstructured text corresponds to advice or a recommendation?"

The advice text corresponds to advice from the medical practitioner and can include but is not limited to recommended courses of action. As can be seen in FIG. 2, item 44a in field 44 corresponds to phrase 34c in field 34.

The display also includes structured results field 46 and structure advice field 48. The structured results and structures advice fields 46, 48 correspond to a coded representation of the information contained in fields 42, 44 and 34. Thus, systems such as the systems described below in conjunction with FIGS. 3-6 identify pertinent information in unstructured text and provide a coded representation of the pertinent information.

The information in fields 42-28 is automatically generated by a system and technique such as those described herein which analyzes unstructured text (e.g. such as the text in field 34) by performing processing which is the same as or similar to the processing described above in conjunction with FIG. 1. The structured results and advice fields can contain automatically determined clinically positive findings, yield, medical advice and recommendation rates for referring physicians, patient cohorts and radiologists. A display such as the display 26 may be included in a system similar to the system to be described below in conjunction with FIG. 3.

A system operating in accordance with the techniques described above in conjunction with FIG. 1 can process a relatively large number of reports very rapidly while automatically determining clinically positive findings, yield, medical advice and recommendation rates for referring physicians, patient cohorts and radiologists. Such information can be automatically displayed in the structured results and advice fields of a display such as the display show in FIG. 2. Thus, the display 26 includes a so-called unstructured portion (e.g. field 34) as well as a so-called structured portion (e.g. fields 46, 48) in which compact, efficient, and informative representations of an unstructured report (e.g. as represented by the text in field 34) are provided.

It should appreciated that while the display of FIG. 2 corresponds to a display for a radiology report, the display can be adapted for other types of medical reports and non-medical reports.

Figure 3:
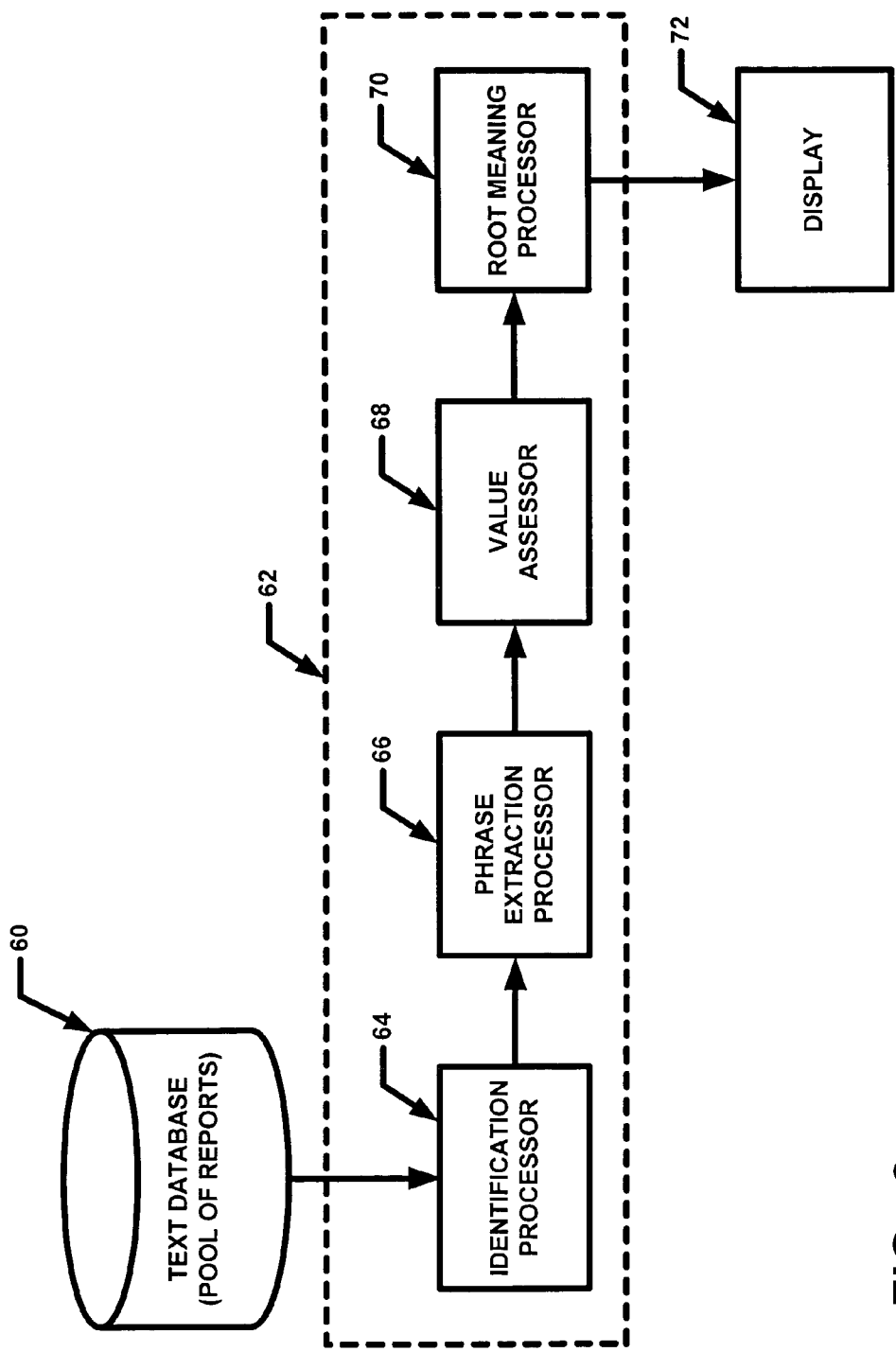
FIG. 3 is a block diagram of a system for processing text to identify phrases of value.

Referring now to FIG. 3, a system for processing text includes a text database 60 from which text is provided to a text processing system 62 (also referred to herein as a LEXIMER system). The text processing system identifies a phrase contained within the text, extracts the phrase from the text, determines if the phrase has value and in response to the phrase having value, reducing the phrase to a codified root meaning. The processing system 62 is coupled to a display 72.

The text processing system 62 includes an identification processor 64 coupled to a phrase extraction processor 66. The phrase extraction processor is coupled to a value assessor 68 which in turn is coupled to a root meaning processor 70.

In one particular embodiment, the LEXIMER system and technique were implemented as an automatic search engine for classifying radiology reports into two categories. One category of reports were those reports that contained clinically significant findings (designated as $F_T$) and those reports that contained recommendations for subsequent action (designated as $R_T$). One hundred consecutive, de-identified CT and MRI reports, accessed from report database, have been independently assessed by two radiologists and by the LEXIMER for $F_T$ and $R_T$. Accuracy of the LEXIMER system for classifying reports into $F_T$ and $R_T$ was assessed using appropriate statistical tests. Additional 1,000 CT, MR, US and Radiography reports (de-identified) were analyzed using the LEXIMER system.

The results showed significant linear correlation between the LEXIMER system and blinded radiologists for classifying radiology reports into $F_T$ and $R_T$ categories ($p<0.05$). The LEXIMER system correctly classified 50/54 $F_T$ (4 false negative, 2 false positive, 94% accuracy). The LEXIMER system correctly identified 16/16 $R_T$ (3 false positive, 97% accuracy). The time for a 1000 report search with the LEXIMER system was 14 seconds. Thus, the LEXIMER system is an accurate and rapid automated engine to assess clinically significant findings and recommendations in unstructured radiology reports. The system offers tremendous opportunity for analysis of large radiology report database to study patterns of imaging utilization by physicians, disease distribution, radiology self-referral and radiologist performance metrics.

Figure 4:
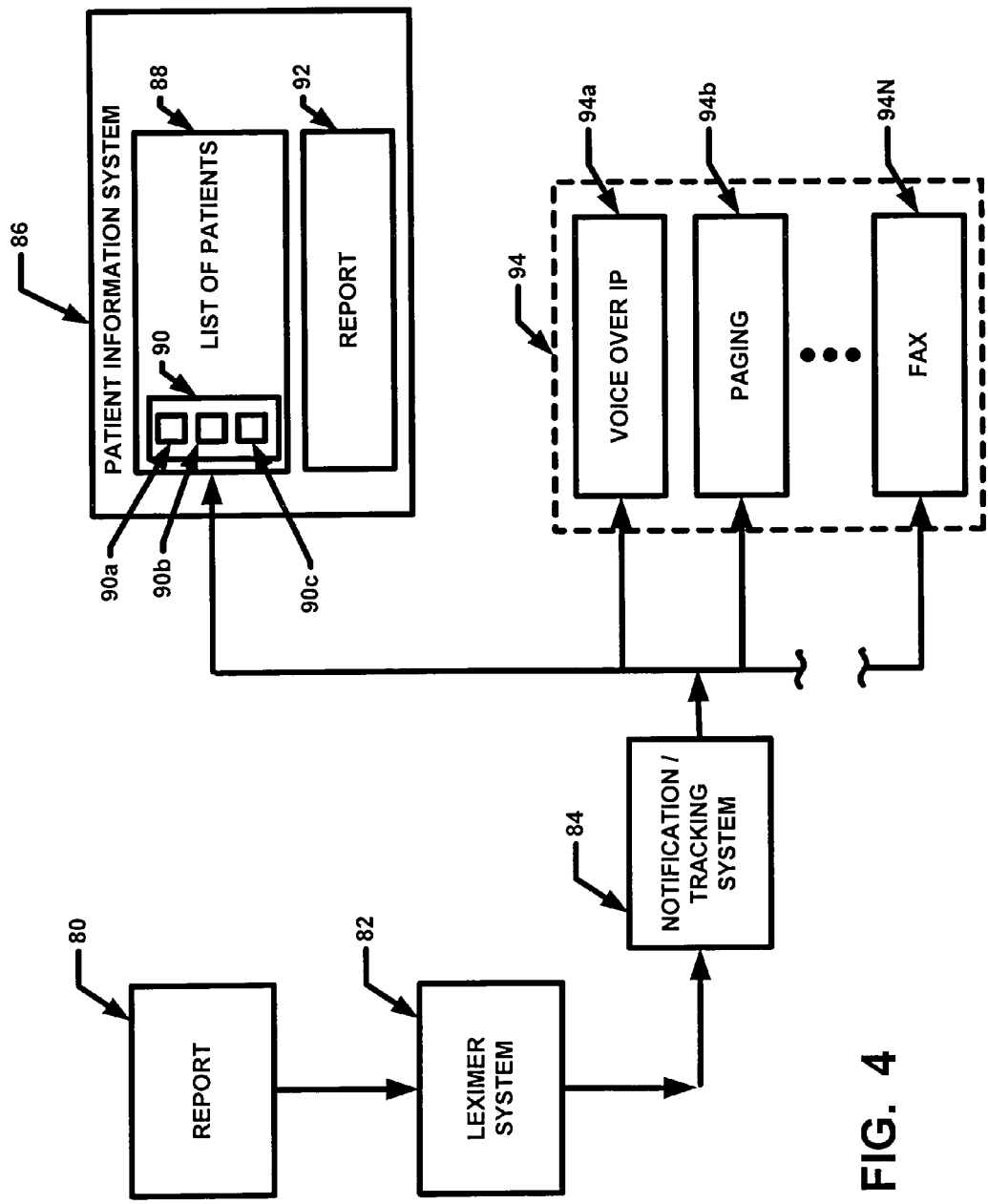
FIG. 4 is a block diagram of a system for processing a medical report to extract information and provide the information on a display.

Referring now to FIG. 4, a report 80 such as a medical or other type of report is provided to a text processing system or Leximer system 82 (where Leximer is the series of computer algorithms used to process the text into codified meaning as described above). The Leximer system 82 is coupled to a notification and tracking system 84 which is in turn coupled to a patient information system 86 and a means 94 for communicating with a medical practitioner (e.g. a doctor or other medical practitioner).

The patient information system 86 may correspond, for example, to an electronic medical record (EMR) which includes a list of patients 88 and a checklist 90 having one or more check boxes 90a-90c. By checking one of the boxes 90a-90c, a single report 92 can be displayed on a display. The means 94 can include one or more communication means such as a voice over IP system 94a, a paging system 94b and a facsimile system 94N. Thus, in this application, the Leximer system is utilized to provide a notification/tracking system.

Figure 5:
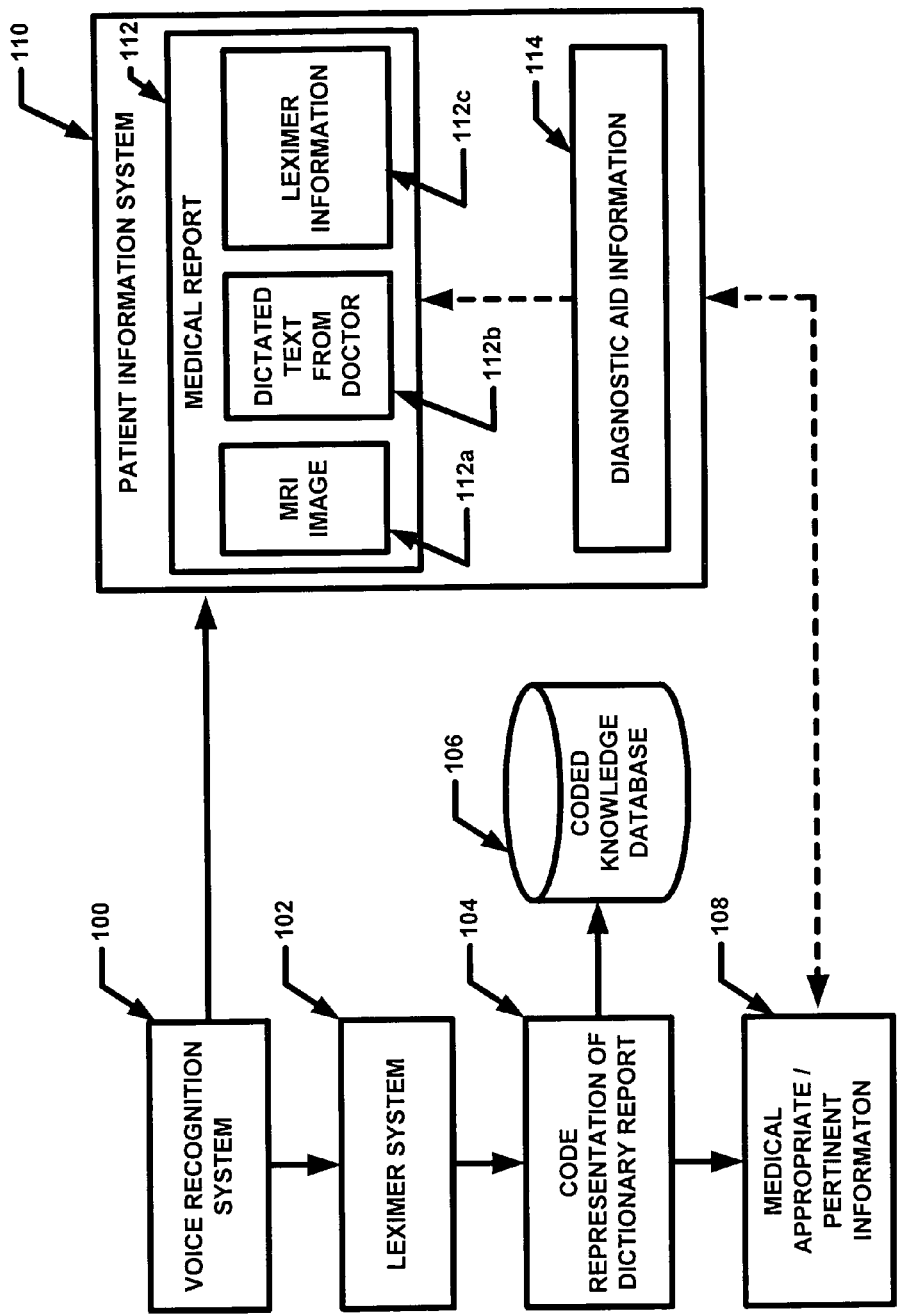
FIG. 5 is a block diagram of a system which accepts information from a voice recognition system, processes the information and provides the information to a patient information system.

Referring now to FIG. 5, a voice recognition system 100 is coupled to a text processing system or Leximer system 102 (where Leximer is the series of computer algorithms used to process the text into codified meaning as described above). The code representation report 104 is linked to a coded knowledge database 106 resulting in the ability to display relevant real time medical knowledge in the form of 108, a medical appropriate/pertinent information system.

The voice recognition system 100 and the medical appropriate/pertinent information system 108 are each coupled to a patient information system 110 so that real time display of the relevant medical knowledge can occur. The patient information system 110 includes a medical report portion 112 and a diagnostic information portion 114. The medical report may include, for example, an MRI image 112a, dictated text from a doctor or other medical practitioner 112b and Leximer generated information 112c. As an example, a physician may be using voice recognition to deliver a long unstructured report containing a finding of a mass in the adrenal gland. The Leximer system would extract the relevant phrase of meaning and subsequently codify the terms 'mass' and 'adrenal gland'. The system would then link to a medical knowledge database and extract information relevant to these findings such as the differential diagnosis of an 'Adrenal Gland Mass".

Figure 6:
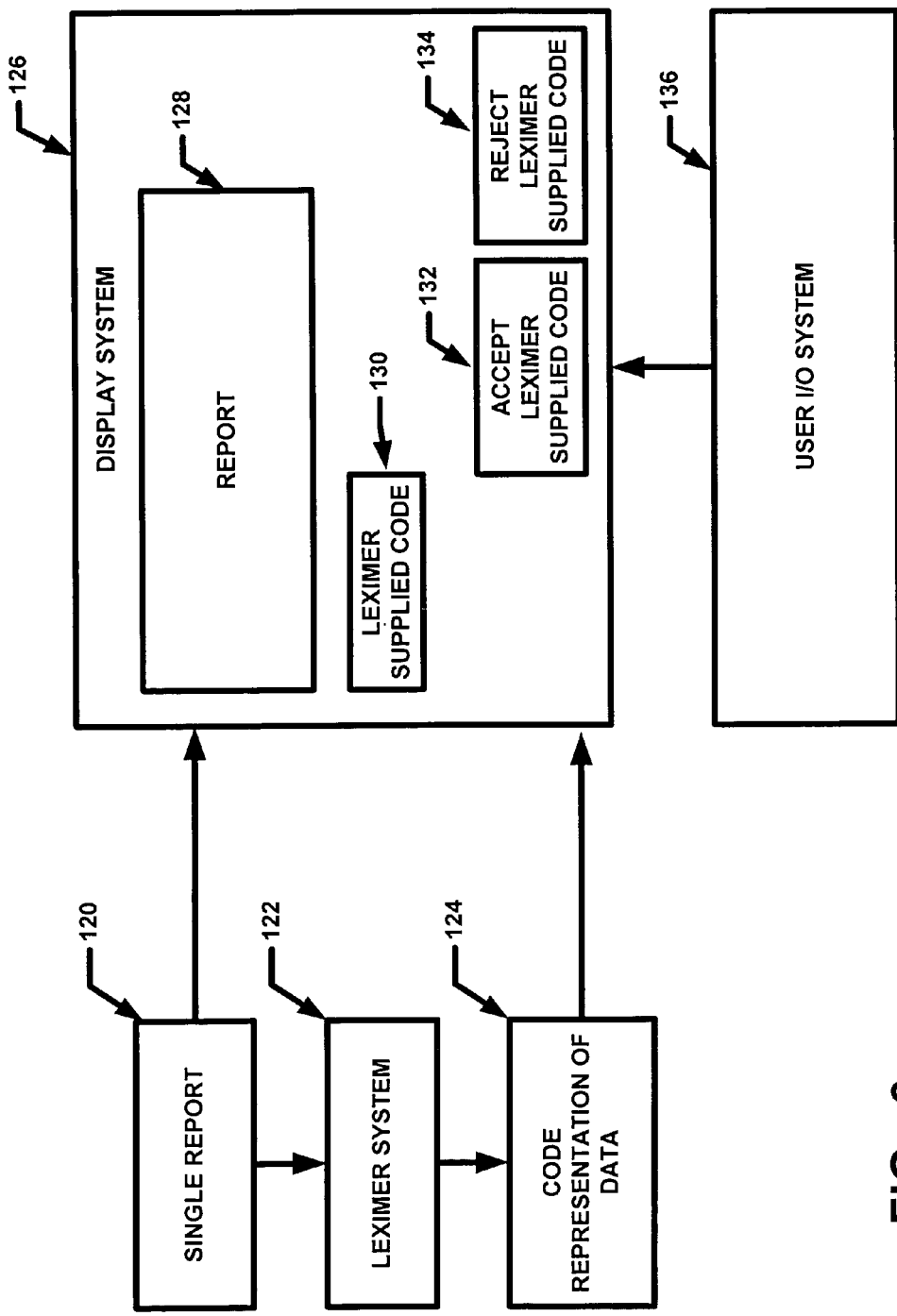
FIG. 6 is a block diagram of a system for automatically processing medical reports and generating medical codes for use in medical billing systems.

Referring now to FIG. 6, a report 120 for a single patient is provided to a text processing system or Leximer system 122. The system 122 processes the text of the report to provide a code representation of the data 124, such as 'Adrenal Gland Mass'. The Leximer system 122, through the coded representation 124, is coupled to a display system 126.

The display system 126 includes a report 128 and a Leximer supplied code 130. A user of the system, via user input/output (I/O) system 136 can decide to accept or reject the Leximer supplied code 130 via controls 132, 134.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

What is claimed is:

1. A computer method, comprising:
   processing automatically medical text in a medical report within a medical field using a computer, the processing comprising:
   identifying medical phrases contained within the medical text;
   extracting the medical phrases from the medical text;
   determining which of the medical phrases are valued medical phrases, a valued medical phrase includes content having a corresponding value in a lexicon of relevant terminology corresponding to the medical field, the valued medical phrase being either a medical finding or a medical recommendation;
reducing each valued medical phrase to one or more medical codes in the medical field; the one or more medical codes being medical identifiers; and
rendering in a first group medical codes corresponding to the medical finding; and
rendering in a second group separate from the first group medical codes corresponding to the medical recommendation,
wherein processing automatically the medical text in the medical report further comprises generating a lexicon-based hierarchical decision tree for the medical field by assigning each valued medical phrase to a location in the lexicon-based hierarchical decision tree.

2. The computer method of claim 1, wherein reducing each valued medical phrase to one or more medical codes in the medical field comprises reducing each valued medical phrase to one or more standard medical codes in the medical field.

3. The computer method of claim 1, wherein determining which of the medical phrases are valued medical phrases comprises determining which of the medical phrases are valued medical phrases including content having a corresponding value in a previously trained lexicon of relevant terminology corresponding to the medical field.

4. The computer method of claim 1 wherein rendering in the first group medical codes corresponding to the medical finding comprises displaying on a screen the first group,
wherein rendering in the second group medical codes corresponding to the medical recommendation comprises displaying on the screen the second group.

5. The computer method of claim 1, wherein determining which of the medical phrases are valued medical phrases comprises determining which of the medical phrases are valued medical phrases including content having a corresponding value in a lexicon of radiological terms.

6. The computer method of claim 1, wherein processing automatically the medical text within the medical field using the computer comprises processing automatically the medical text within radiology.

7. The computer method of claim 1, wherein reducing each valued medical phrase to one or more medical codes in the medical field comprises reducing each valued medical phrase to one or more radiology codes in radiology.

8. The computer method of claim 1, wherein reducing each valued medical phrase to one or more medical codes in the medical field comprises reducing each valued medical phrase to one or more codes from at least one of Current Procedural Terminology, Fourth Revision (CPT4), International Classification of Diseases, Ninth Revision (ICD9), Systematized Nomenclature of Medicine (SNOWMED), a lexicon of radiological terms and Unified Medical Language System (UMLS).

9. The computer method of claim 1, further comprising transcribing dictated words into the medical text using a voice recognition and transcription system.

10. An apparatus, comprising:
hardware circuitry configured to process automatically medical text in a medical report within a medical field, the circuitry configured to process automatically medical text comprises circuitry configured to:
identify medical phrases contained within the medical text;
extract the medical phrases from the medical text;
determine which of the medical phrases are valued medical phrases, a valued medical phrase includes content having a corresponding value in a lexicon of relevant terminology corresponding to the medical field, the valued medical phrase being either a medical finding or a medical recommendation;
reduce each valued medical phrase to one or more medical codes in the medical field; the one or more medical codes being medical identifiers; and
render in a first group medical codes corresponding to the medical finding; and
render in a second group separate from the first group medical codes corresponding to the medical recommendation,
wherein the circuitry comprises a processor, and
wherein the circuitry configured to process automatically the medical text in the medical report further comprises circuitry configured to generate a lexicon-based hierarchical decision tree for the medical field by assigning each valued medical phrase to a location in the lexicon-based hierarchical decision tree.

11. The apparatus of claim 10, wherein the one or more medical codes in the medical field comprises one or more standard medical codes in the medical field.

12. The apparatus of claim 10, wherein the trained lexicon of relevant terminology corresponding to the medical field comprises a previously trained lexicon of relevant terminology corresponding to the medical field.

13. The apparatus of claim 11, wherein the circuitry configured to render in the first group medical codes corresponding to the medical finding comprises circuitry configured to display on a screen the first group; and
wherein the circuitry configured to render in the second group medical codes corresponding to the medical recommendation comprises circuitry configured to display on the screen the second group.

14. The apparatus of claim 11, wherein the a lexicon of relevant terminology comprises a lexicon of radiological terms.

15. The apparatus of claim 11, wherein the medical field is radiology.

16. The apparatus of claim 11, wherein the one or more medical codes in the medical field comprises one or more radiology codes in radiology.

17. The apparatus of claim 11, wherein the one or more medical codes in the medical field comprises one or more codes from at least one of Current Procedural Terminology, Fourth Revision (CPT4), International Classification of Diseases, Ninth Revision (ICD9), Systematized Nomenclature of Medicine (SNOWMED), a lexicon of radiological terms, or Unified Medical Language System (UMLS).

18. The apparatus of claim 11, further comprising circuitry configured to transcribe dictated words into the medical text.

19. A computer method, comprising:
processing automatically medical text in a radiology report using a computer, the processing comprising:
identifying medical phrases contained within the medical text;
extracting the medical phrases from the medical text;
determining which of the medical phrases are valued medical phrases, a valued medical phrase includes content having a corresponding value in a lexicon of relevant terminology in radiology, the valued medical phrase being either a medical finding or a medical recommendation;
reducing each valued medical phrase to one or more radiology codes in radiology from at least one of Current Procedural Terminology, Fourth Revision (CPT4), International Classification of Diseases, Ninth Revision (ICD9), Systematized Nomenclature of Medicine (SNOWMED), a lexicon of radiological terms, or Unified Medical Language System (UMLS); the one or more medical codes being medical identifiers; and rendering in a first group medical codes corresponding to the medical finding; and rendering in a second group separate from the first group medical codes corresponding to the medical recommendation, wherein processing automatically the medical text in the radiology report further comprises generating a lexicon-based hierarchical decision tree for radiology by assigning each valued medical phrase to a location in the lexicon-based hierarchical decision tree.

20. The computer method of claim 19 wherein rendering in the first group medical codes corresponding to the medical finding comprises displaying on a screen the first group, wherein rendering in the second group medical codes corresponding to the medical recommendation comprises displaying on the screen the second group.

21. The computer method of claim 19, further comprising transcribing dictated words into the medical text using a voice recognition and transcription system.

22. The computer method of claim 19, wherein the circuitry configured to determine which of the medical phrases are valued medical phrases comprises circuitry configured to determine which of the medical phrases are valued medical phrases including content having a corresponding value in a lexicon of radiological terms.

23. An apparatus, comprising:
hardware circuitry configured to process automatically medical text from a radiology report, the circuitry configured to process automatically medical text comprises circuitry configured to:
identify medical phrases contained within the medical text;
extract the medical phrases from the medical text;
determine which of the medical phrases are valued medical phrases, a valued medical phrase includes content having a corresponding value in a lexicon of relevant terminology in radiology, the valued medical phrase being either a medical finding or a medical recommendation;
reduce each valued medical phrase to one or more medical codes in radiology from at least one of Current Procedural Terminology, Fourth Revision (CPT4), International Classification of Diseases, Ninth Revision (ICD9), Systematized Nomenclature of Medicine (SNOWMED), a lexicon of radiological terms, or Unified Medical Language System (UMLS); the one or more medical codes being medical identifiers; and
render in a first group medical codes corresponding to the medical finding; and
render in a second group separate from the first group medical codes corresponding to the medical recommendation,
wherein the circuitry comprises a processor,
wherein the circuitry configured to process automatically the medical text from the radiology report further comprises circuitry configured to generate a lexicon-based hierarchical decision tree for radiology by assigning each valued medical phrase to a location in the lexicon-based hierarchical decision tree.

24. The apparatus of claim 23, wherein the circuitry configured to render in the first group medical codes corresponding to the medical finding comprises circuitry configured to display on a screen the first group; and wherein the circuitry configured to render in the second group medical codes corresponding to the medical recommendation comprises circuitry configured to display on the screen the second group.

25. The apparatus of claim 23, further comprising circuitry configured to transcribe dictated words into the medical text.

26. The apparatus of claim 23 wherein the apparatus is configured to process automatically medical text in fourteen seconds from a thousand radiology reports in to one of reports comprising clinically significant findings or reports comprising recommendations for subsequent action.

* * * * *

UNITED STATES PATENT AND TRADEMARK OFFICE
CERTIFICATE OF CORRECTION

| | | |
|---|---|---|
| PATENT NO. | : 8,756,234 B1 | Page 1 of 1 |
| APPLICATION NO. | : 10/989598 | |
| DATED | : June 17, 2014 | |
| INVENTOR(S) | : Keith J. Dreyer | |

It is certified that error appears in the above-identified patent and that said Letters Patent is hereby corrected as shown below:

In the specification

Column 2, Line 61, delete "encoded" and replace with --encode--.

Column 4, Line 28, delete "here in" and replace with --herein--.

Column 5, Line 41, delete "such a" and replace with --such as--.

Column 7, Line 12, delete "show" and replace with --shown--.

Signed and Sealed this
Twenty-fourth Day of November, 2015

Michelle K. Lee
*Director of the United States Patent and Trademark Office*